United States Patent
Thornberry (10) Patent No.: US 11,269,086 B2
(45) Date of Patent: Mar. 8, 2022

(54) SYSTEM AND METHOD FOR RADON DETECTION

(71) Applicant: Ultimo Global Holdings, LLC, Wilmington, DE (US)

(72) Inventor: Phillip Nathan Thornberry, Carmel, IN (US)

(73) Assignee: Ultimo Global Holdings LLC, Wilmington, DE (US)

( * ) Notice: Subject to any disclaimer, the term of this patent is extended or adjusted under 35 U.S.C. 154(b) by 187 days.

(21) Appl. No.: 16/747,909

(22) Filed: Jan. 21, 2020

(65) Prior Publication Data

US 2021/0223411 A1   Jul. 22, 2021

(51) Int. Cl.

| | |
|---|---|
| *G01T 1/178* | (2006.01) |
| *G08B 21/12* | (2006.01) |
| *G01T 1/185* | (2006.01) |
| *G08B 21/14* | (2006.01) |
| *H01J 47/02* | (2006.01) |
| *G01N 33/00* | (2006.01) |
| *F24F 110/68* | (2018.01) |

(52) U.S. Cl.
CPC ......... *G01T 1/178* (2013.01); *G01N 33/0055* (2013.01); *G01T 1/185* (2013.01); *G08B 21/12* (2013.01); *G08B 21/14* (2013.01); *H01J 47/02* (2013.01); *F24F 2110/68* (2018.01); *Y10S 250/02* (2013.01)

(58) Field of Classification Search
CPC ..... G01T 1/178; G01T 1/185; G01N 33/0055; G08B 21/12; G08B 21/14; H01J 47/02; F24F 2110/68; Y10S 250/02
See application file for complete search history.

(56) References Cited

U.S. PATENT DOCUMENTS

| | | | | |
|---|---|---|---|---|
| 4,800,272 A | * | 1/1989 | Harley | G01T 1/11 250/253 |
| 6,288,400 B1 | * | 9/2001 | Negro | G01N 27/66 250/255 |

(Continued)

FOREIGN PATENT DOCUMENTS

| | | | | |
|---|---|---|---|---|
| CN | 106504468 A | * | 3/2017 | G08B 19/00 |

OTHER PUBLICATIONS

TianJin Fire—CN 106504468 A—Google Patents English obtained Sep. 17, 2021 (Year: 2021).*

*Primary Examiner* — David P Porta
*Assistant Examiner* — Jeremy S Valentiner
(74) *Attorney, Agent, or Firm* — Woodard Emhardt Henry Reeves & Wagner LLP (57) ABSTRACT

The present disclosure provides a system for detection and measuring of a radioactive gas within a target environment. In certain embodiments, the system comprises a data processing system and a monitoring device disposed within the target environment. In some forms the monitoring device comprises: a radiation sensor configured to detect the concentration of a radioactive gas in the target environment, a transmitter electrically coupled to the radiation sensor and configured for transmitting a signal to the data processing system, and a receiver for receiving signals from the data processing system, wherein the monitoring device is configured to detect the concentration of the radioactive gas at least every twenty minutes.

17 Claims, 6 Drawing Sheets

(56) References Cited

U.S. PATENT DOCUMENTS

| | | | |
|---|---|---|---|
| 7,019,637 B1* | 3/2006 | Johnson ................. | G08B 21/12 |
| | | | 340/506 |
| 2004/0129890 A1* | 7/2004 | Berman ................. | G01T 1/178 |
| | | | 250/380 |
| 2007/0044539 A1* | 3/2007 | Sabol .................... | G06Q 10/06 |
| | | | 73/19.01 |

* cited by examiner

SYSTEM AND METHOD FOR RADON DETECTION

BACKGROUND

There are many commercially available systems for detecting radioactive gases such as radon. Such systems are designed to be deployed on site to detect levels of radioactive gases over a period of time. It should be appreciated that human intervention in monitoring procedures, whether an intended or unintended (e.g., tampering with the device) step of the procedures, have been known to introduce errors in the obtained results. Additionally, it should be appreciated that it is often cumbersome, inconvenient and/or inefficient for personnel (e.g., the technician) to go back to the testing site in order to perform final readings and/or retrieve a monitoring device for measurement at the test facility. In addition, not every attempt to test an environment of interest is initially successful. A number of factors including, for example, failure of the monitoring device itself, misuse or tampering by non-certified persons at the test site may result in the need for another test. Such misuse or tampering can be, for example, an intentional or unintentional interruption resulting from a non-technician altering one or more parameters of the test procedures. As a result, a qualified technician would be required to revisit the test site, install a new device (or correct parameters of the current device) and initiate another test cycle. A need therefore exists for a radioactive gas-monitoring device, which minimizes direct intervention by limiting the number of times that a technician returns to the test site, and which can provide alerts when a test has been interrupted.

Accordingly, the present invention provides improved methods and apparatus for collecting, detecting and measuring radioactive gases (e.g., radon) and suspended aerosols within an environment of interest that addresses the above described and other perceived deficiencies in conventional monitoring devices. Thus, there is a need for improvement in this field.

SUMMARY

In certain aspects, the present disclosure provides unique systems and methods for the detecting and/or measuring a radioactive gas. In accordance with some forms of the invention, such systems and methods are configured to allow for early detection and quantification of the level of radioactive gas present in a target environment. Accordingly, in one embodiment the present disclosure provides a system for detection and measuring of a radioactive gas within a target environment, the system comprising: a data processing system and a monitoring device disposed within said environment. In some forms the monitoring device comprises a radiation sensor configured to detect the concentration of a radioactive gas in the target environment, a transmitter electrically coupled to the radiation sensor and configured for transmitting a signal to the data processing system, and a receiver for receiving signals from the data processing system, wherein said monitoring device is configured to detect the concentration of the radioactive gas at least every twenty minutes. In certain embodiments, the radioactive gas comprises radon. In some forms, the monitoring device is configured to detect the concentration of the radioactive gas at least every 15 minutes. In accordance with certain inventive variants, the transmitter comprise a Wi-Fi transmitter. In some forms, the transmitter comprises a cellular transmitter. In certain embodiments the monitoring device further comprise a battery configured to power the monitoring device for at least 48 hours. In certain embodiments, the monitoring device further comprises a GPS receiver, and the transmitter is configured to transmit information from the GPS receiver to the data processing system. In some forms, the monitoring device further comprises an accelerometer, and the transmitter is configured to transmit information from the accelerometer to the data processing system. In certain embodiments the monitoring device further comprises one or more of the following: a temperature sensor, a humidity sensor, and/or a pressure sensor, and the transmitter is configured to transmit information from the temperature sensor, humidity sensor, and/or pressure sensor to the data processing system. In accordance with some forms, the monitoring device comprises a local storage device.

Further forms, objects, features, aspects, benefits, advantages, and embodiments of the present invention will become apparent from a detailed description and drawings provided herewith.

DESCRIPTION OF THE SELECTED EMBODIMENTS

For the purpose of promoting an understanding of the principles of the invention, reference will now be made to the embodiments illustrated in the drawings and specific language will be used to describe the same. It will nevertheless be understood that no limitation of the scope of the invention is thereby intended. Any alterations and further modifications in the described embodiments, and any further applications of the principles of the invention as described herein are contemplated as would normally occur to one skilled in the art to which the invention relates. One embodiment of the invention is shown in great detail, although it will be apparent to those skilled in the relevant art that some features that are not relevant to the present invention may not be shown for the sake of clarity.

As used herein the term "radioactive gas" refers to any gaseous material containing radioactive atoms. In preferred embodiments, the systems and methods described herein relate to naturally occurring radioactive gas, for example radon, thoron, and actinon.

As used herein the term "radon" refers to the chemical element having the atomic number 86, with the symbol Rn.

Under normal conditions, radon is a gas and may be easily inhaled posing a health risk to those exposed.

As used herein the term "radiation sensor" refers to any suitable radiation detection means known in the art. In certain embodiments, the systems described herein utilize a pulsed ionization chamber to measure radon levels in a target environment. It should be appreciated that other radiation detection concepts may be utilized that equally produce an electrical signal that, in accordance with the present disclosure, correspond to an amount of radioactive gas (e.g. radon) in a target environment. In certain embodiments, a radiation sensor as used herein may have a sensitivity of at least 30 cph/pCi/l.

As used herein "transmitter" refers to a system or apparatus configured to transmit data. In one example, a transmitter may comprise a WiFi or other Wireless Local Area Network (WLAN) or cellular transmitter suitable to transmit data.

As used herein the term "GPS receiver" refers to a receiver configured to receive transmission from Global Positioning System (GPS) satellites to determine the receiver's precise location (e.g. latitude and longitude). In some forms a GPS receiver is also configured to transmit such positional data, via the transmitter or otherwise, to the data processing system.

As used herein the term "accelerometer" refers to a sensor configured to measure proper acceleration. In some forms, an accelerometer is configured to transmit such acceleration data, via the transmitter or otherwise, to the data processing system.

As used herein the term "working level" (WL) refers to any combination of short-lived radon daughters (for radon-222: polonium-218, lead-214, bismuth-214, and polonium-214; and for radon-220: polonium-216, lead-212, bismuth-212, and polonium-212) in 1 liter of air that will result in the ultimate emission of $1.3 \times 10^5$ MeV of potential alpha particle energy pCi/L) in air.

As used herein the term "working level month" (WLM) refers to exposure of an individual to 1 WL for every 170 hours.

Figure 1:
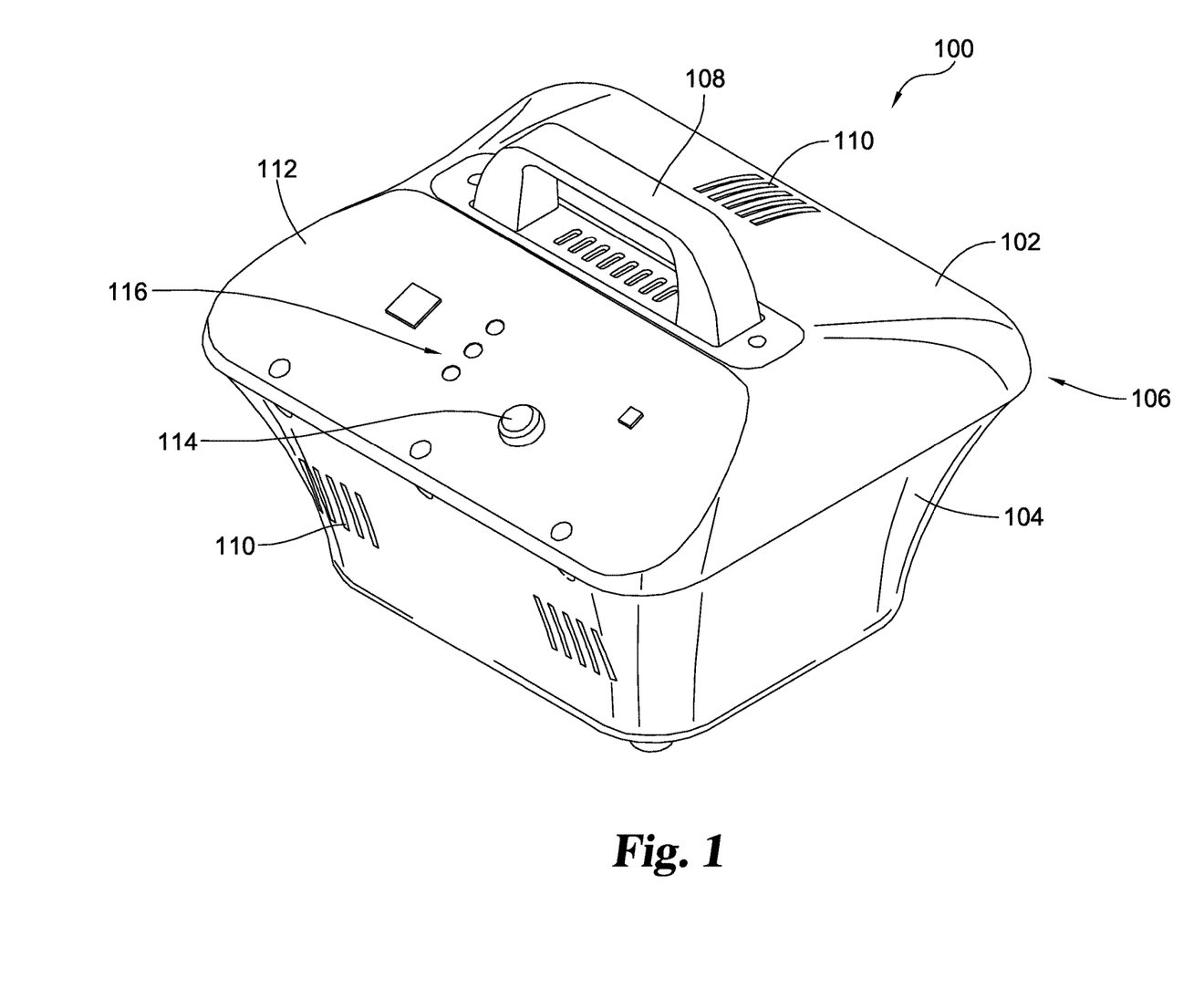
FIG. 1 is a perspective view of one embodiment of a monitoring device as described herein.

With reference to FIG. 1, illustrated is one embodiment of a monitoring device 100 for use with the disclosed system for detecting and measuring a radioactive gas. In the illustrated embodiment, the monitoring device comprises an upper portion 102 secured to a lower portion 104 together forming an enclosure 106. In certain embodiments, the enclosure may house one or more of the additional components described herein. In the illustrated embodiment, the enclosure includes a handle 108. In certain embodiments, the enclosure includes a plurality of ventilation openings 110, which allow air and other gases (e.g. radioactive gases) to flow into the monitoring device.

In accordance with certain embodiments, the monitoring device may include a control panel 112. In some forms, the control panel is configured to allow direct control of the monitoring device. In certain embodiments, the monitoring device includes a power switch 114. In accordance with certain embodiments, the monitoring device comprises one or more status indicators 116. The status indicators may be any suitable means of communicating the status of the device, for example in certain embodiments the status indicator(s) may comprise an LCD display, a needle gauge, and or a light. In a preferred embodiment, the status indicator(s) comprise one or more LED lights. The status indicators may be used to communicate various states of the device, for example whether the device is powered, whether the device has detected an error, and/or whether the device is currently running a test. In accordance with some forms, the device is configured to provide calibration reminders. For example, in some forms a reminder is displayed by the device, for example on an LCD display or other indicator, to indicate that the device should be calibrated. In accordance with some forms, the device is configured to display a reminder at least two weeks in advance of calibration. In this way the device allows for completion of a testing cycle without interruption for calibration.

Figure 2:
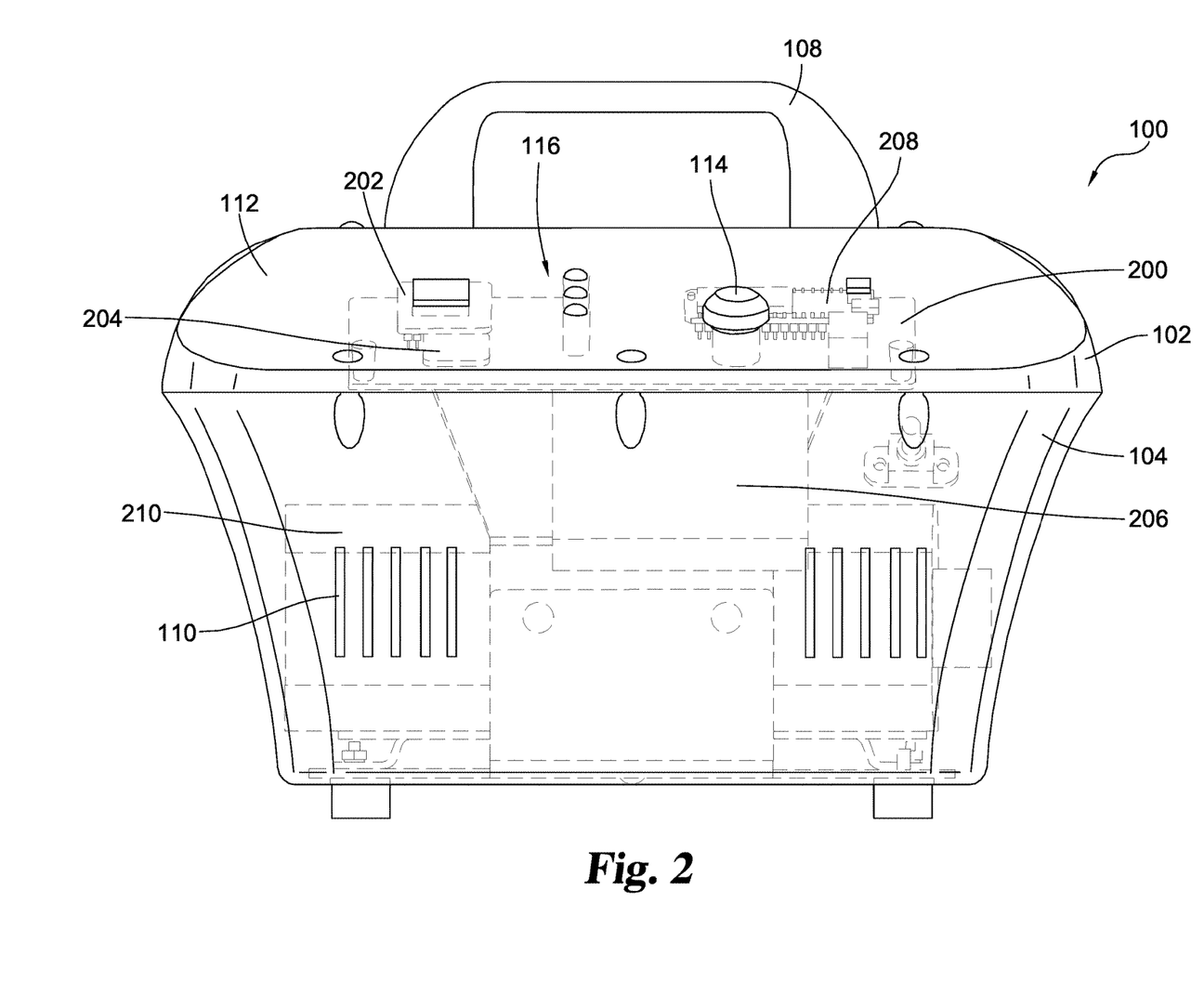
FIG. 2 is a front view of one embodiment of a monitoring device as described herein. Exemplary internal components of the monitoring device are shown using dashed lines.
Figure 3:
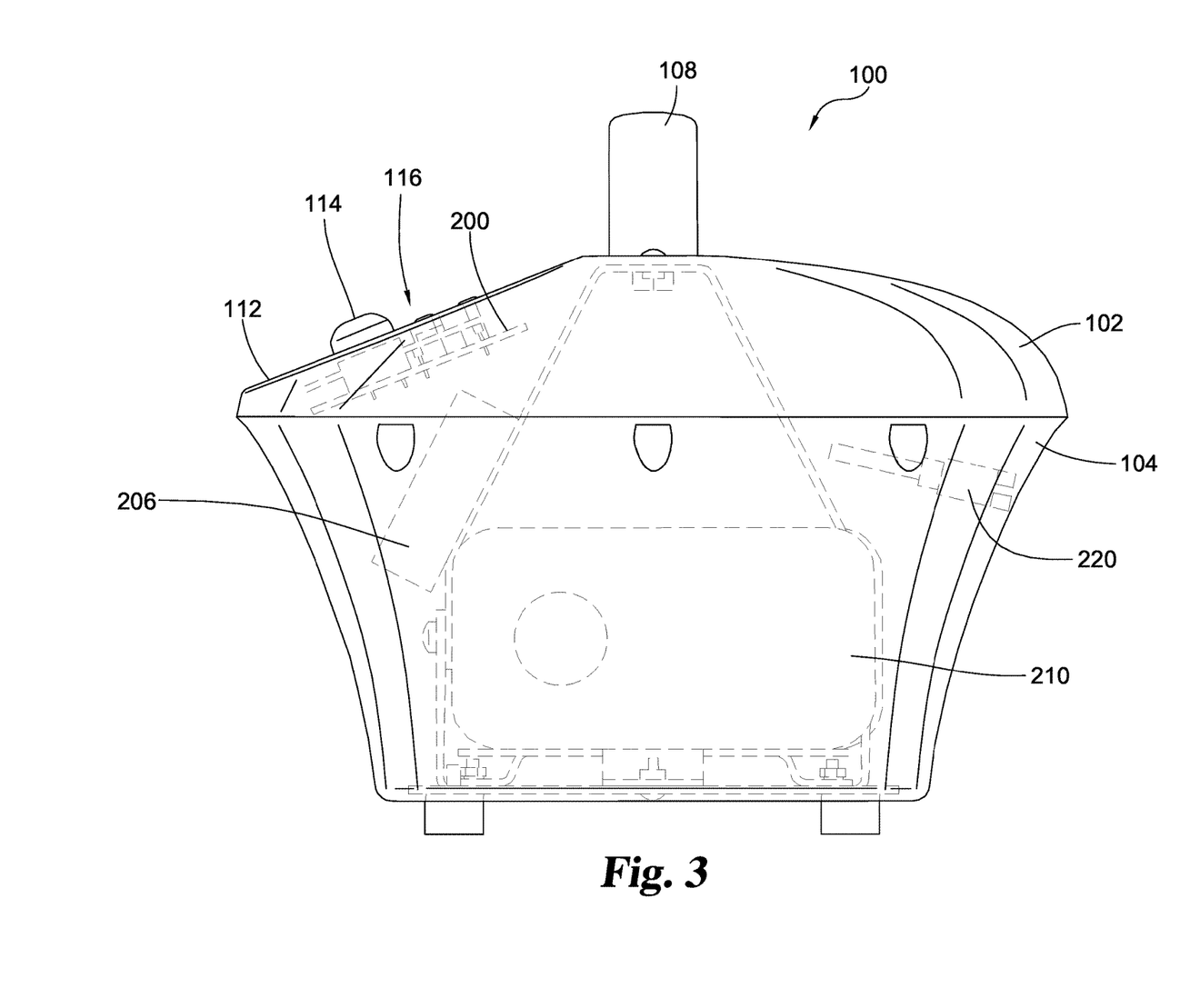
FIG. 3 is a side view of one embodiment of a monitoring device as described herein. Exemplary internal components of the monitoring device are shown using dashed lines.
Figure 4:
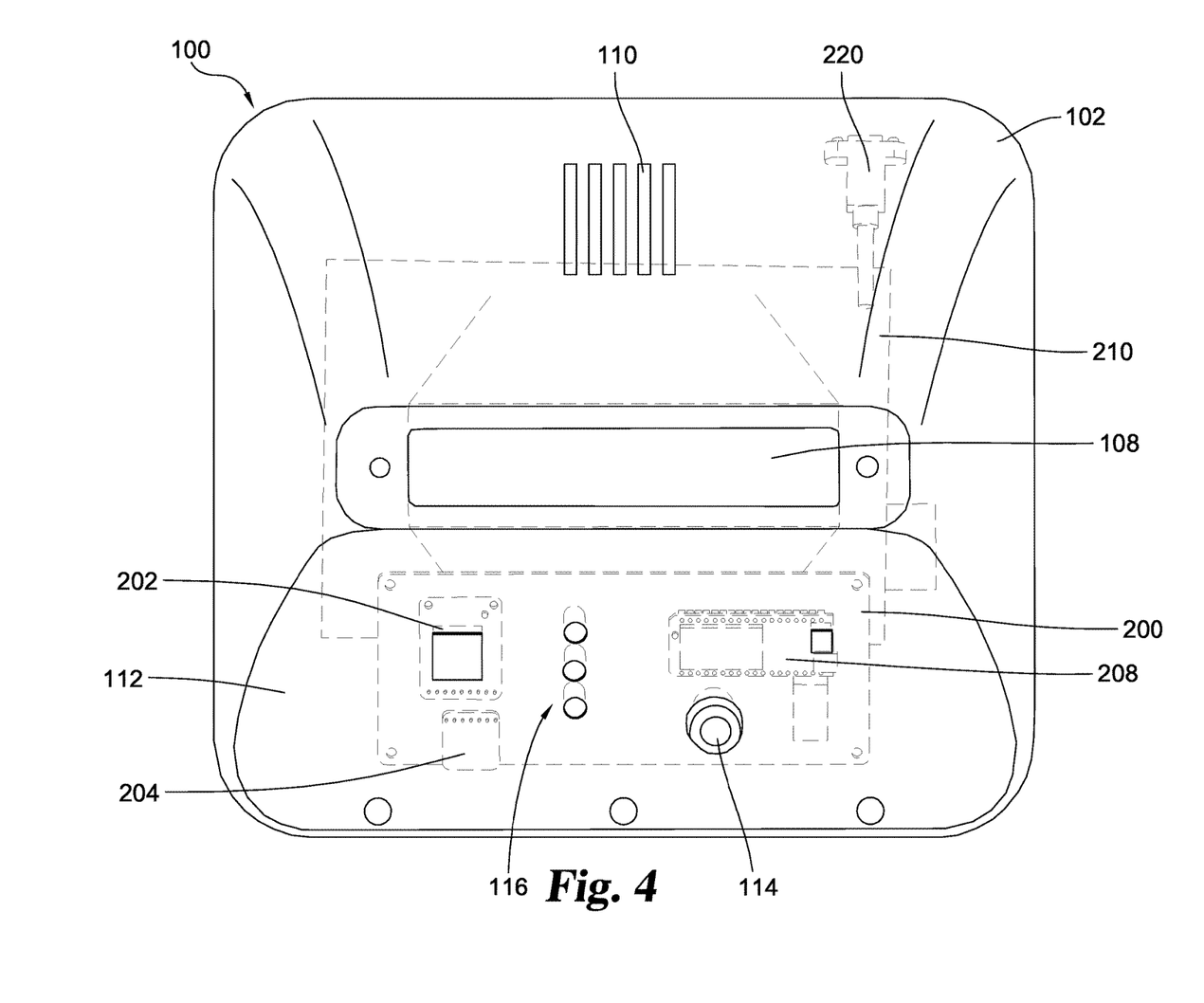
FIG. 4 is a top-down view of one embodiment of a monitoring device as described herein. Exemplary internal components of the monitoring device are shown using dashed lines.

Turning now to FIGS. 2-4, shown are front (FIG. 2), side (FIG. 3), and top-down (FIG. 4) views of one embodiment of a monitoring device 100. Exemplary internal components of the monitoring device are shown using dashed lines. Thus in accordance with certain embodiments, a monitoring device for use with the disclosed system may include a control board 200. In some forms, the control board is operably connected to a global positioning system (GPS) receiver 202. In certain embodiments, the monitoring device comprises a radon sensor 210 operably connected to the control board. In accordance with certain embodiments, the control board is operably connected to one or more environmental sensors 204. Environmental sensors may be configured to sense aspects of the environment in which the device is deployed such as: temperature, humidity, and/or air pressure. In some forms, the monitoring device comprises a battery 206 operably connected to the control board. In accordance with some forms, the monitoring devices comprises a main processor 208. Certain inventive variants may also include one or more data input ports 220, in preferred embodiments the data input port comprises a USB port operably connected to the control board.

As disclosed herein the monitoring devices of the present disclosure may further comprise one or more transmitters operably connected to the control board. In certain embodiments, the monitoring device comprises a Wi-Fi transmitter operably connected to the control board. In certain embodiments, the monitoring device comprises a cellular control configured to transmit data over a cellular connection. In certain embodiments one or more of the transmitters is configured to receive signals (e.g. via Wi-Fi and/or cellular transmission).

In certain embodiments, a monitoring device as disclosed herein may comprise one or more accelerometers. As used herein the term "accelerometer" refers to a device configured to detect and/or measure acceleration. Thus in some forms, the present disclosure provides for a monitoring device comprising an accelerometer, the accelerometer may be operably connected to the control board. In certain instances, the accelerometer may report movement of the device during testing which may indicate tampering and/or failure of the test.

Thus in accordance with some forms, the present disclosure provides a system for the detection and measuring of a radioactive gas within a target environment. In certain embodiments, the system comprises a data processing system. As used herein "data processing system" refers to a remote processing center configured to receive transmission from one or more monitoring devices as described herein. The data processing system receives signals (e.g. radioactive gas level data), executes one or more processes as outlined herein, and transmits additional data back to the monitoring device(s). In this way, a data processing system may comprise a centralized server or cloud based system configured to receive and transmit signals from remote monitoring devices. Thus, in some forms the system is configured to detect the presence and/or concentration of a target radioactive gas in a target environment and transmit the detected concentration to a remote data processing center. For example, in some forms a monitoring device as disclosed herein may be configured to transmit one or more readings (e.g. radon, humidity, accelerometer data and/or temperature) every 60 minutes, preferably every 30 minutes, even more preferably every 10 minutes. In accordance with certain inventive variants, the system transmits an average reading taken over time, for example over 60 minutes, preferably over 30 minutes, even more preferably over 10 minutes.

The present disclosure also provides for worldwide access to the data transmitted to the data processing center. In this way, the system is configured to allow a user to access the data (e.g. the presence and/or concentration of a radioactive gas such as radon, temperature, humidity, air pressure, accelerometer data, date, time, and/or GPS data) remotely.

Figure 5:
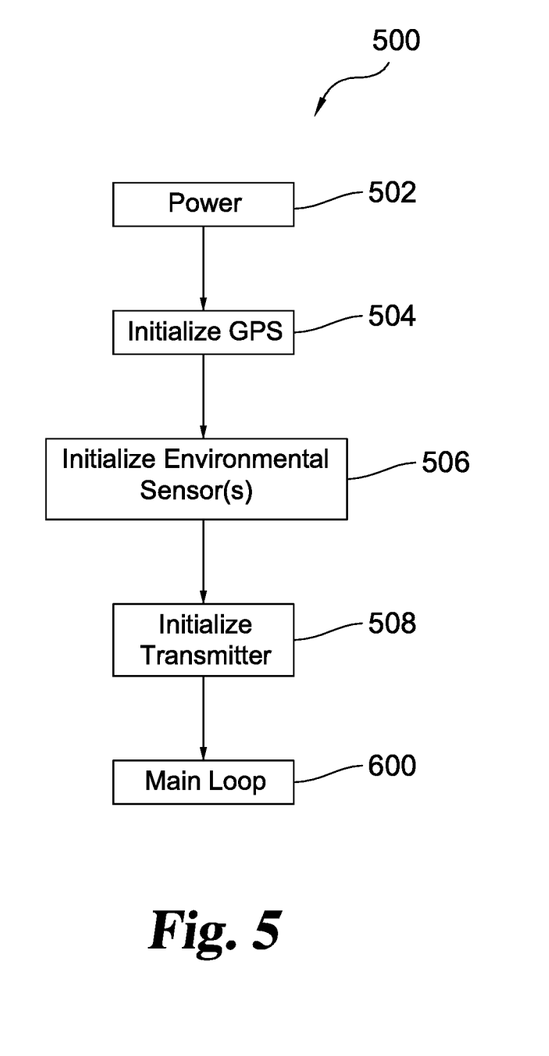
FIG. 5 is a flow diagram illustrating one embodiment of a system for detection and measuring of a radioactive gas as disclosed herein.

With reference to FIG. 5, in certain embodiments, the system for detecting and measuring a radioactive gas provided herein comprises an initiation stage 500. In some forms, the device is powered on 502. The device may be powered on remotely or directly by a user, for example in some forms the power switch is pressed or toggled to activate the device. In certain embodiments, the GPS is initialized 504. In certain embodiments, one or more environmental sensors is initialized 506. In certain embodiments, the one or more transmitters is initialized 508. The term "initialized" as used herein means to bring a component to its ready state, wherein it is ready to perform its function (e.g. measure and report the temperature, or send and/or receive a data transmission). In certain embodiments, a main loop 600 is initialized.

Figure 6:
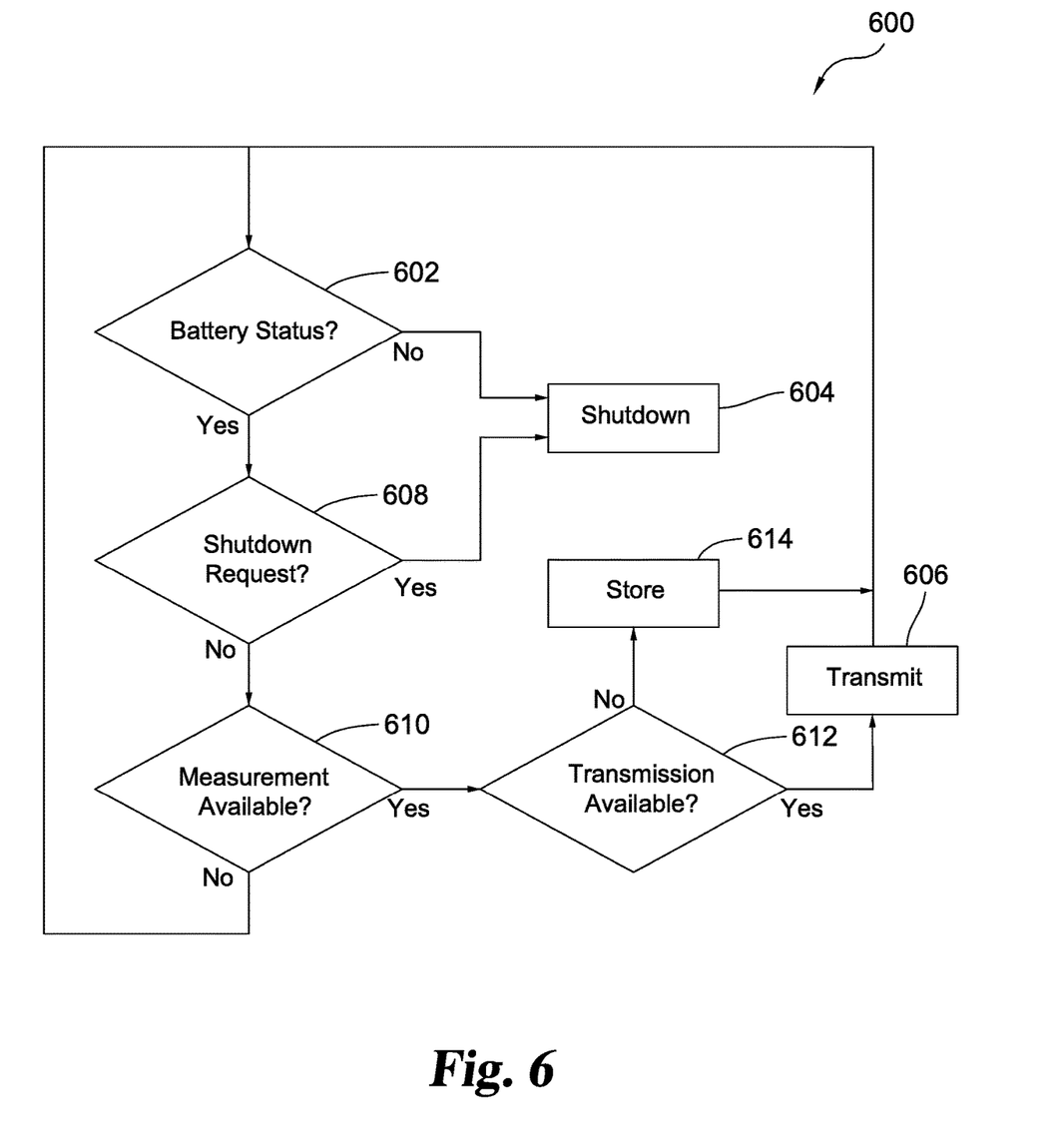
FIG. 6 is a flow diagram illustrating one embodiment of a system for detection and measuring of a radioactive gas as disclosed herein.

FIG. 6 is a flow diagram illustrating one embodiment of main loop 600 in accordance with some forms of practicing the disclosed system and method. Certain embodiments include a battery check stage 602. In certain embodiments, if the battery has insufficient remaining charge the system is shutdown 604. Certain embodiments include a shutdown request check stage 608. In some forms, a shutdown request may be sent remotely, for example via the transmitter, or directly via the power switch. If a shutdown request is detected the system is shutdown 604. Certain embodiments include a measurement check stage 610. The measurement check stage may include a check for the availability of any of the variable measured by the device. These variables include any of those discussed herein, for example: the presence and/or concentration of a radioactive gas (e.g. radon), temperature, humidity, air pressure, accelerometer data and/or GPS data.

Certain embodiments include a transmission available stage 612. In some forms the transmission available stage utilizes one or more of the transmitters (e.g. cellular, Wi-Fi, and/or Bluetooth) to check for an active connection to the data processing system. In accordance with certain embodiments if an active connection is available measurement data is then transmitted to the data processing system in transmit stage 606. In some forms one or more of the following data is sent to the data processing system: the presence and/or concentration of a radioactive gas (e.g. radon), temperature, humidity, air pressure, accelerometer data, date, time, and/or GPS data. Certain embodiments include a store stage 614. In some forms, if no active connection to the data processing system is available one or more measurements are stored on a local storage device. In accordance with certain embodiments, all measurements are locally stored, including those measurements transmitted to the data processing system. In certain embodiments, the system stores measurements until an active connection is established, at which point all stored measurements are transmitted to the data processing system.

Thus in accordance with certain embodiments the system is configured to register a test failure. In some forms, the failure may be indicated by the one or more status indicators and/or may be transmitted to the data processing system. In certain embodiments, a test failure is detected by a sufficient change in one or more of the measured parameters. For example, a sudden change in temperature, pressure, and/or GPS data may indicted that the area and/or monitoring device may have been tampered with during testing and that the test results may be inaccurate. In certain embodiments, the system is configured to request system shutdown upon detecting of a test failure.

In certain embodiments, the system for detection and measuring of a radioactive gas described herein is configured to measure one or more of the variables measured by the device at least once every 30 minutes, preferably at least once every 20 minutes, even more preferably at least once every 15 minutes. It is within the scope of the disclosure for a system as described herein which is configured to measure the levels of radioactive gas (e.g. radon) present in the target environment at least once every 30 minutes, 20 minutes, 15 minutes, 10 minutes, and/or 5 minutes. In some forms at least one or more of the variables is continuously monitored. As disclosed above, the variables measured by the device include any of those discussed herein, for example: the presence and/or concentration of a radioactive gas (e.g. radon), temperature, humidity, air pressure, accelerometer data and/or GPS data. Thus in accordance with some forms the systems disclosed herein are configured to measure the levels of radioactive gas at multiple intervals during a testing period. For example, a testing period may be about 36 hours long, and the device may be configured to transmit and/or store measurement data for more than 140 measurements during the testing period. In certain embodiments the system is configured to store and/or transmit measurement data at least twice per hour, preferably at least three times per hour, more preferably at least 4 times per hour during the testing period.

In certain embodiments, the monitoring device is configured to receive transmission from the data processing system. In some forms, the monitoring device may receive a software update remotely from the data processing system, such updates may enhance the ability of the device to detect additional environmental parameters.

In accordance with certain inventive variants the systems disclosed herein are configured to transmit each of the measurements to the data processing system, such that the system is able to determine the level of radon in the target environment within about 48 hours of the test start time, preferably within about 36 hours, more preferably within about 24 hours of the test start time. In some forms, the system provided herein is able to determine the level of radon in the target environment with about 12 hours of the test start time. Applicants have developed this system so as to allow for rapid determination of radioactive gas levels in a target environment so as to allow for more rapid remediation efforts if necessary.

The presently disclosed system may also be configured to track duplicate tests performed at the same target location. In some forms, a user may input duplicate test data. In certain embodiments, two or more devices are activated at a target location. In accordance with certain embodiments, a user may input that the second device is a duplicate test. In this way, the system of the present disclosure allows for efficient tracking of duplicate test data. In certain embodiments, the system may be configured to notify a technician placing the test that a duplicate test should be placed. In some forms, the data processing system is configured to generate a relative percent difference (RPD) chart. In this way, the system ensures that the device is functioning properly by establishing control limits.

In accordance with certain embodiments, the systems of the present disclosure may also be configured to determine the working level month (WLM) exposure of an individual (e.g. technician). In accordance with some forms, each device is configured to determine the working level (WL) exposure associated with obtaining the measurement. The device is configured to transmit the WL and/or WLM data to the data processing system. In some forms, the WLM of an individual may thus be tracked by the data processing system to alert of over exposure to one or more radioactive gases. In this way, the present system provides a safety mechanism for individuals testing from radioactive gases.

While the invention has been illustrated and described in detail in the drawings and foregoing description, the same is to be considered as illustrative and not restrictive in character, it being understood that only the preferred embodiment has been shown and described and that all changes, equivalents, and modifications that come within the spirit of the inventions defined by following claims are desired to be protected. All publications, patents, and patent applications cited in this specification are herein incorporated by reference as if each individual publication, patent, or patent application were specifically and individually indicated to be incorporated by reference and set forth in its entirety herein.

The invention claimed is:

1. A system for detection and measuring of a radioactive gas within a target environment, the system comprising:
    a data processing system; and
    a monitoring device, said monitoring device comprising:
        a radiation sensor configured to detect the concentration of a radioactive gas in the target environment;
        a battery configured to supply power to the monitoring device for at least 48 hours;
        a transmitter electrically coupled to said radiation sensor and configured for transmitting a signal to said data processing system, wherein said signal comprises information regarding the concentration of the radioactive gas; and
        a receiver for receiving signals from said data processing system, wherein said monitoring device is configured to detect the concentration of the radioactive gas at least every twenty minutes.

2. The system for detection and measuring of a radioactive gas within a target environment of claim 1, wherein said radioactive gas comprises radon.

3. The system for detection and measuring of a radioactive gas within a target environment of claim 1, wherein said monitoring device is configured to detect the concentration of the radioactive gas at least every 15 minutes.

4. The system for detection and measuring of a radioactive gas within a target environment of claim 1, wherein said radiation sensor comprises a pulsed ionization chamber.

5. The system for detection and measuring of a radioactive gas within a target environment of claim 1, wherein said radiation sensor has a sensitivity of at least 30 cph/pCi/l.

6. The system for detection and measuring of a radioactive gas within a target environment of claim 1, wherein said transmitter comprises a WiFi transmitter.

7. The system for detection and measuring of a radioactive gas within a target environment of claim 1, wherein said transmitter comprises a cellular transmitter.

8. The system for detection and measuring of a radioactive gas within a target environment of claim 1, wherein said monitoring device further comprises a GPS receiver, and wherein said transmitter is configured to transmit information from said GPS receiver to said data processing system.

9. The system for detection and measuring of a radioactive gas within a target environment of claim 1, wherein said monitoring device further comprises an accelerometer, and wherein said transmitter is configured to transmit information from said accelerometer to said data processing system.

10. The system of claim 1, wherein said monitoring device further comprises one or more of the following: a temperature sensor, a humidity sensor, and/or a pressure sensor.

11. The system of claim 10, wherein the system is configured to register a test failure in response to sudden change detected by the temperature sensor, the humidity sensor, and/or the pressure sensor.

12. The system of claim 1, wherein said monitoring device further comprises a local data storage device.

13. The system of claim 2, wherein the system is configured to determine the level of radon within the target environment within 12 hours of test initialization.

14. The system of claim 1, wherein the system is configured to detect the concentration of radioactive gas during a testing period of at least 24 hours.

15. The system of claim 14, wherein the system is configured to transmit the detected concentration of radioactive gas in the target environment to the data processing system at least twice per hour during the testing period.

16. The system of claim 1, wherein the system is configured to track duplicate test results.

17. The system of claim 1, wherein the system is configured to display a notification that device calibration is needed.

* * * * *

(12) EX PARTE REEXAMINATION CERTIFICATE (12478th)
United States Patent
Thornberry

(10) Number: US 11,269,086 C1
(45) Certificate Issued: Dec. 21, 2023

(54) SYSTEM AND METHOD FOR RADON DETECTION

(71) Applicant: Ultimo Global Holdings, LLC, Wilmington, DE (US)

(72) Inventor: Phillip Nathan Thornberry, Carmel, IN (US)

(73) Assignee: ULTIMO GLOBAL HOLDINGS, LLC, Carmel, IN (US)

Reexamination Request:
No. 90/020,152, Jan. 18, 2023

Reexamination Certificate for:
Patent No.: 11,269,086
Issued: Mar. 8, 2022
Appl. No.: 16/747,909
Filed: Jan. 21, 2020

(51) Int. Cl.
*G01T 1/178* (2006.01)
*G01N 33/00* (2006.01)
*H01J 47/02* (2006.01)
*G08B 21/14* (2006.01)
*G01T 1/185* (2006.01)
*G08B 21/12* (2006.01)
*F24F 110/68* (2018.01)

(52) U.S. Cl.
CPC ......... *G01T 1/178* (2013.01); *G01N 33/0055* (2013.01); *G01T 1/185* (2013.01); *G08B 21/12* (2013.01); *G08B 21/14* (2013.01); *H01J 47/02* (2013.01); *F24F 2110/68* (2018.01); *Y10S 250/02* (2013.01)

(58) Field of Classification Search
None
See application file for complete search history.

(56) References Cited

To view the complete listing of prior art documents cited during the proceeding for Reexamination Control Number 90/020,152, please refer to the USPTO's Patent Electronic System.

*Primary Examiner* — James A Menefee

(57) ABSTRACT

The present disclosure provides a system for detection and measuring of a radioactive gas within a target environment. In certain embodiments, the system comprises a data processing system and a monitoring device disposed within the target environment. In some forms the monitoring device comprises: a radiation sensor configured to detect the concentration of a radioactive gas in the target environment, a transmitter electrically coupled to the radiation sensor and configured for transmitting a signal to the data processing system, and a receiver for receiving signals from the data processing system, wherein the monitoring device is configured to detect the concentration of the radioactive gas at least every twenty minutes.

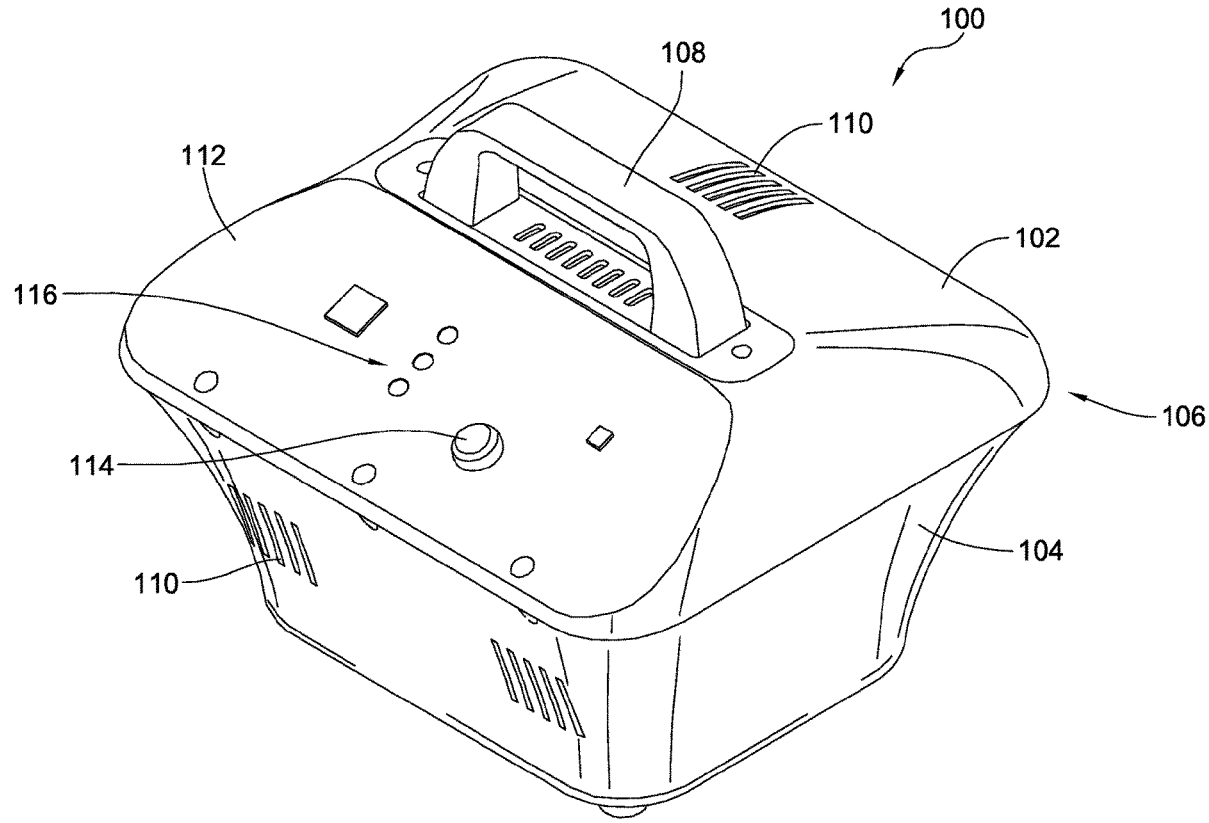

EX PARTE REEXAMINATION CERTIFICATE

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

Claim 2 is cancelled.

Claims 1, 13 and 15 are determined to be patentable as amended.

Claims 3-12, 14, 16 and 17, dependent on an amended claim, are determined to be patentable.

New claims 18 and 19 are added and determined to be patentable.

1. A system for detection and measuring of a radioactive gas within a target environment, the system comprising:
    a data processing system *configured to receive data from one or more monitoring devices, and transmit commands to one or more monitoring devices, wherein the data processing system is configured to allow a user to access the data and send commands remotely*; and
    a monitoring device, said monitoring device comprising:
        a radiation sensor configured to detect the concentration of [a radioactive] *radon* gas in the target environment;
        a battery configured to supply power to the monitoring device for at least 48 hours;
        a transmitter electrically coupled to said radiation sensor and configured for transmitting [signal] *data* to said data processing system, wherein said [signal] *data* comprises*:*
            information regarding the concentration of [the radioactive] *radon* gas, *wherein the device is configured to transmit the detected concentration of radon gas in the target environment at least twice per hour during the testing period*; and
        a receiver for receiving signals from said data processing system, wherein said *commands comprise:*
            *a power on command, the monitoring device being configured to power on in response to the power on command; and*
            *a shutdown request command, the monitoring device being configured to shut down in response to the shutdown request command; and*
        *wherein said* monitoring device is configured to detect the concentration of [the radioactive] *radon* gas at least every twenty minutes.

13. The system of claim [2] *1*, wherein the system is configured to determine the level of radon within the target environment within 12 hours of test initialization.

15. The system of claim [14] *1*, wherein the system is configured to transmit the detected concentration of radioactive gas in the target environment to the data processing system at least [twice] *four times* per hour during the testing period.

*18. The system of claim 12, wherein the system is configured to test for an active connection between the transmitter and the data processing system, wherein if no active connection is available the measurement is stored on the local storage device, and wherein when an active connection is established any stored measurements are transmitted.*

*19. The system of claim 1, wherein said monitoring device further comprises a GPS receiver, a temperature sensor, a humidity sensor, and a pressure sensor, and wherein said commands further comprise a an initialize command for one or more of the accelerometer, the GPS receiver, the temperature sensor, the humidity sensor, and the pressure sensor.*

* * * * *